United States Patent
Matthíasson et al.

(10) Patent No.: US 10,945,964 B2
(45) Date of Patent: Mar. 16, 2021

(54) MICROENCAPSULATED CHITOSAN, METHODS OF MAKING AND METHODS FOR THE USE THEREOF

(71) Applicant: PRIMEX EHF., Siglufjordur (IS)

(72) Inventors: Einar Matthíasson, Siglufjordur (IS); Sigrídur Vigdis Vigfúsdóttir, Siglufjordur (IS); Hélène L. Lauzon, Siglufjordur (IS); Ólafur Stefánsson, Siglufjordur (IS); Gudnÿ Helga Kristjánsdóttir, Siglufjordur (IS)

(73) Assignee: PRIMEX EHF., Siglufjordur (IS)

( * ) Notice: Subject to any disclaimer, the term of this patent is extended or adjusted under 35 U.S.C. 154(b) by 0 days.

(21) Appl. No.: 16/492,107

(22) PCT Filed: Mar. 5, 2018

(86) PCT No.: PCT/IB2018/051410
§ 371 (c)(1),
(2) Date: Sep. 6, 2019

(87) PCT Pub. No.: WO2018/163053
PCT Pub. Date: Sep. 13, 2018

(65) Prior Publication Data
US 2020/0054572 A1 Feb. 20, 2020

Related U.S. Application Data

(60) Provisional application No. 62/468,274, filed on Mar. 7, 2017.

(51) Int. Cl.
*A61K 9/50* (2006.01)
*A23P 10/30* (2016.01)
(Continued)

(52) U.S. Cl.
CPC .......... *A61K 9/5042* (2013.01); *A21D 13/06* (2013.01); *A23L 33/28* (2016.08); *A23P 10/30* (2016.08);
(Continued)

(58) Field of Classification Search
CPC .. A61K 9/5042; A61K 9/0056; A61K 31/722; A23P 10/30; A23L 33/28; A21D 21/06; A23V 2002/00; A61P 3/06
See application file for complete search history.

(56) References Cited

U.S. PATENT DOCUMENTS

2010/0048508 A1 2/2010 Ben-Shalom

FOREIGN PATENT DOCUMENTS

JP 2004-51615 * 2/2004
JP 2004-51615 A 2/2004
(Continued)

OTHER PUBLICATIONS

Lorenzo-Lamosa, Design of Microencapsulated Chitosan for Colonic Drug Delivery, Journal of Controlled Release, vol. 52, No. 1-2, pp. 109-118. (Year: 1998).*
(Continued)

*Primary Examiner* — Carlos A Azpuru
(74) *Attorney, Agent, or Firm* — Kilpatrick Townsend & Stockton LLP

(57) ABSTRACT

Provided herein are microencapsulated chitosan materials and formulations containing same, methods of making such formulations, and methods of using such formulations. Application of a microencapsulation coating on chitosan materials and formulations containing same renders possible the use of chitosan materials for different, novel chitosan-based dietary applications with the primary aim to decrease intestinal absorption of fat and enhance overall health, without interfering with or reducing food palatability. The
(Continued)

present invention provides methods to microencapsulate highly effective chitosan or chitosan salts to moderate their interaction with food components and mask any off-flavors and off-tastes but allow rapid chitosan solubilization under gastric acid conditions and simultaneous binding of ingested lipids. Chitosan contemplated for use herein is preferably of high quality with high fat-binding capacity, and its source is preferably of crustacean origin.

14 Claims, 3 Drawing Sheets

(51) Int. Cl.
    *A23L 33/28*     (2016.01)
    *A21D 13/06*     (2017.01)
    *A61K 9/00*     (2006.01)
    *A61K 31/722*     (2006.01)

(52) U.S. Cl.
    CPC .......... *A61K 9/0056* (2013.01); *A61K 31/722* (2013.01); *A23V 2002/00* (2013.01)

(56) References Cited

FOREIGN PATENT DOCUMENTS

| JP | 2004-262860 A | 9/2004 |
|---|---|---|
| WO | 01/82724 A2 * | 11/2001 |
| WO | 2001082724 A2 | 11/2001 |

OTHER PUBLICATIONS

Lorenzo-Lamosa et al.: "Design of microencapsulated chitosan microspheres for colonic drug delivery", Journal of Controlled Release, Elsevier, Amsterdam, NL, vol. 52, No. 1-2, Mar. 1998, pp. 109-118, XP004113659, ISSN:0168-3659.
Database WPI, Week 200429, Thomson Scientific, London, GB, AN 2004-308523, XP002780873, 2 pages.
Database WPI, Week 200469, Thomson Scientific, London, GB, AN 2004-702707, XP002780874, 4 pages.
PCT/IB2018/051410 International Search Report and Written Opinion, dated May 23, 2018, 14 pages.

* cited by examiner (a)

(b)

(c)

(d)

MICROENCAPSULATED CHITOSAN, METHODS OF MAKING AND METHODS FOR THE USE THEREOF

CROSS-REFERENCE TO RELATED APPLICATIONS

This application is a 371 U.S. National Phase of PCT International Patent Application No. PCT/IB2018/051410, filed on Mar. 5, 2018, which claims benefit and priority to U.S. provisional patent application No. 62/468,274, filed on Mar. 7, 2017, the disclosures of which are each incorporated by reference herein in their entirety.

FIELD OF THE INVENTION

The present disclosure relates to microencapsulated chitosan materials and formulations containing same. In certain embodiments, the present disclosure relates to methods of making such formulations, and methods of using such formulations.

BACKGROUND OF THE INVENTION

The information provided herein and references cited are provided solely to assist the understanding of the reader, and does not constitute an admission that any of the references or information is prior art to the present invention.

Chitosan is a N-acetyl-glucosamine polysaccharide obtained from the deacetylation of chitin, a natural fiber found in some invertebrates, such as crustaceans' exoskeleton and insects' cuticles, and the cell wall of fungi. Chitin with a degree of deacetylation (DDA)>50% is considered as chitosan. Chitin is insoluble in most organic solvents while chitosan is soluble in dilute acidic solutions below pH 6.0. This is due to the presence of the amino group becoming reactive upon deacetylation. The main parameters influencing the characteristics of chitosan are its molecular weight (MW) and its DDA. Due to the diversity of the sources of chitosan, and to the fact that it is commercially available with a wide range of DDA and MW, each of which may affect chitosan properties, it is recognized that the source and processing procedures used in the manufacturing of chitosan will affect its bioactivity.

Some fibers are known to reduce the intestinal absorption of fat and cholesterol in the diet, mainly following the entrapment caused by a viscous polysaccharide solution or the increased viscosity of the polysaccharide once in stomach acid. Chitosan, being the only amino-polysaccharide naturally occurring on earth, has a structural advantage compared to other fibers since it becomes cationic under acidic conditions (pH <6). This renders possible the attraction of anionic substances, such as fatty acids and bile acids, to chitosan resulting in a spontaneous formation of an insoluble chitosan salt (Muzzarelli et al. 2006—Carbohydrate Polymers 66: 363-71). In addition, the hydrophobic nature of chitosan will allow cholesterol and other neutral lipids to bind via hydrophobic interactions.

A recent study (Rodriguez & Albertengo 2005—Bioscience, Biotechnology, and Biochemistry 69(11): 2057-62) evaluated the interaction of chitosan and a common food oil, sunflower oil, using a chemical experimental model of the human digestive tract (gastric and duodenal environment). The results indicated that chitosan dissolves under gastric condition and emulsifies oil, before forming a flocculus at the higher duodenal pH (6.5-7.5). The flocculus formed entraps dietary oil and prevents lipid absorption through the intestinal wall, leading to the oil being excreted with the feces and a lower calorie intake. Therefore, chitosan is considered as being lipid-lowering and hypocholesterolemic, as it can reduce fat absorption and enterohepatic bile acid circulation. Chitosan attraction and binding to fatty acids, neutral sterols and bile acids by electrostatic and hydrophobic forces has been proposed as the main mechanism.

The fat-binding properties of chitosan products can vary due to their ability to solubilize rapidly or more slowly under stomach acid conditions. Triglyceride binding is evaluated with the material solubilized in a hydrochloric acid solution of similar concentration to the gastric secretions present in a fasting stomach. This is followed by mixing solubilized chitosan with a known quantity of oil. The mixture is then neutralized with a carbonate buffer and the precipitation of chitosan entraps the oil into a semi-solid emulsion. The free oil is separated from the bound oil by centrifugation. The bound oil is indirectly quantified and the triglyceride binding capacity of chitosan is calculated as grams of oil bound per gram of chitosan tested.

Chitosan is a common dietary supplement on the market, often offered as a capsule to facilitate its intake and reduce any undesirable off-flavors the product may have. Chitosan products sourced from crustaceans, specifically northern shrimp, and processed to achieve a highly pure and bioactive product have demonstrated enhanced fat-binding properties.

In the dietary supplement industry, chitosan is used to prevent the absorption of dietary fat. Fat complexation, or entrapment, is a function of chitosan's solubility at an acidic pH and insolubility at a basic pH. That is, soluble chitosan mixes with fat and subsequently forms a semi-solid emulsion under basic pH conditions. This chitosan-fat emulsion is resistant to digestion and absorption. Fat-binding properties of chitosan products are hence demonstrated by a test assessing the fat quantity emulsified after a time-related solubilization in acid, mimicking stomach conditions (0.16 N HCl). Rapid acid solubilization is evaluated with a solubilization time of 5 minutes at a pH <2. Upon completion of the test, the quantity of bound fat relates to the ability of the product to rapidly solubilize under simulated gastric conditions and bind fat from a meal upon ingestion. Highly effective chitosan has the ability to rapidly solubilize under simulated gastric conditions and bind high quantity of fat (>50 g oil/g chitosan).

Dietary guidance universally recommends diets higher in fiber for health promotion and disease prevention. Dietary fiber is the main energy source of colonic bacteria which can ferment some fibers and produce short-chain fatty acids (SCFA) (den Besten et al. 2013—J. Lipid Res 54: 2325-40). In the human gut, SCFA are an important source of energy and some are transported to other sites around the body for use. Lin et al. (Lin et al. 2012—PloS 7:e35240) examined the effects of SCFA on body weight, glucose metabolism, and gut hormones in mice and demonstrated that butyrate, propionate, and acetate all protected against diet-induced obesity and insulin resistance. Interestingly, butyrate and propionate, but not acetate, induced gut hormones and reduced food intake. Dietary fibers can therefore be used as prebiotics, i.e. non-digestible food ingredients selectively stimulating the growth and activity of bacterial species in the colon. Accumulating evidence indicates that prebiotics have a diverse range of health benefits, particularly by influencing microbial gut ecology, mineral absorption, laxation, potential anticancer properties, and lipid metabolism, together with anti-inflammatory and other immune effects, including atopic disease. Fermentation processes and SCFA production in the large intestine are believed to contribute to several of these phenomena (Macfarlane & Macfarlane 2011—J. Clin. Gastroenterol. 45:S120-7).

The gut microbiota interact with the host through its metabolites (Conlon & Bird 2015—Nutrients 7: 17-44). Recent findings have indicated that dietary fibers can change at least some portion of the gut microbiota composition (Hamaker & Tuncil 2014—J. Mol. Biol. 426: 3838-50). Some metabolites can damage the gut mucosa, such as indoles, ammonia and amines, while others are beneficial, such as SCFA (Brownlee 2011—Food Hydrocolloids 25: 238-50). In addition to their function as precursors for SCFA, the physicochemical properties of dietary fibers play other important roles in human physiology as well. Dietary fibers are differentiated based on their water solubility, which is related to their structure. The soluble and insoluble nature of dietary fibers contributes to their different technological functionality and physiological effects. In the human body, soluble fibers increase viscosity and reduce the glycemic response and plasma cholesterol, while insoluble fibers are porous, contributing to fecal bulk and decreased intestinal transit time (Roehrig 1988—Food Hydrocolloids 2: 1-18). Dietary fibers have three primary mechanisms in the human digestive tract: bulking, viscosity and fermentation. Chitosan offers a great potential as a dietary fiber since it will first dissolve in stomach acid and become soluble and viscous, behaving like a soluble fiber and can bind fat. Once transiting to the intestine, the higher pH will cause it to gel, trapping the bound fat, contributing to faster transit time and reduced putrefactive activity. Chitosan has been demonstrated to possess several biological properties.

Only a limited number of studies have been conducted to evaluate the prebiotic effect of chitosan on human gut microbiota and some metabolite production. It was shown that a 2-week intake of chitosan (3 g daily for 7 days and then 6 g) led to reduced occurrence of lecithinase-negative clostridia and fecal concentrations of putrefactive products (ammonia, phenol, p-cresol and indole), which resulted in less offensive fecal odours (Terada et al. 1995—Microb. Ecol. Health Dis. 8: 15-21). After 14-day intake, SCFA levels had significantly increased, especially propionic acid formation.

Recent publications indicate the potential for chitosan to modulate the colonic microbiota (Simunek et al. 2006—Folia Microbiol. 51: 306-8; Vernazza et al. 2005—Carb. Polym. 60: 539-45). Changes were also observed in overall bacterial composition and Bifidobacteria subpopulation in response to chitosan intake (3 g daily) after only 2-3 days (Mrazek et al. 2010-Folia Microbiol. 55: 352-8). This was reflected by raised levels of fecal Bacteroides, slightly increased or unchanged levels of Bifidobacterium and a little increase in butyrate-producing bacteria. After termination of the 4-week chitosan treatment, it took only 2 days to reestablish the initial microbiota. Other findings have pointed to the prebiotic effect of chitosan on Bifidobacterium, beneficial for human health (Lee et al. 2002—Anaerobe 8: 319-24). Frequent intake of chitosan may enhance overall health, specifically digestive health. Further, EFSA has concluded that a daily consumption of 3-g chitosan will contribute to the maintenance of normal blood LDL cholesterol concentrations.

SUMMARY OF THE INVENTION

Provided herein are microencapsulated chitosan materials and formulations containing same, methods of making such formulations, and methods of using such formulations. Application of a microencapsulation coating on chitosan materials and formulations containing same renders possible the use of chitosan materials for different, novel chitosan-based dietary applications with the primary aim to decrease intestinal absorption of fat and enhance overall health, without interfering with or reducing food palatability. The present invention provides methods to microencapsulate highly effective chitosan or chitosan salts to moderate their interaction with food components and mask any off-flavors and off-tastes but allow rapid chitosan solubilization under gastric acid conditions and simultaneous binding of ingested lipids. Chitosan contemplated for use herein is preferably of high quality with high fat-binding capacity, and its source is preferably of crustacean origin. The formulations contemplated herein comprise (or consist essentially of) microencapsulated chitosan, used in different applications, specifically new types of chitosan-based dietary supplements, functional or medical foods, contributing to health enhancement, digestion, disease prevention or treatment. Also contemplated by the present invention are such uses in either lipid-rich foods or formulations to reduce their caloric value or as a vector food having the role to introduce chitosan during a meal to provide fiber supplementation and/or contribute to a reduced fat absorption by the body during a meal. Additional alternative uses contemplated herein include the development of new chitosan-based dietary supplements where taste-masking and protection of the microencapsulated chitosan is beneficial.

In a first aspect, the disclosure provides methods of producing microencapsulated chitosan suitable for oral intake from finely divided chitosan material (or salts thereof), said method comprising: (a) applying a suitable coating to said finely divided chitosan material under conditions suitable to create a shell microencapsulating the chitosan material, as pure chitosan or as a salt, thereby protecting same, (b) subjecting the resulting chitosan-coating material combination to conditions suitable to achieve interaction between the finely divided chitosan material and the coating material, (c) optionally rinsing the microencapsulated chitosan product to remove any excess coating material, and (d) a batch or continuous drying process, thereby producing a powder, granules or pellets for wide applications in functional foods and/or dietary supplements.

In a second aspect, the disclosure provides chitosan composition, comprising chitosan or salts thereof, wherein the chitosan or salts thereof are microencapsulated by a coating material. In some embodiments thereof, the chitosan is microencapsulated by a method of the foregoing aspect or any embodiments thereof.

Further aspects and embodiments disclosed herein are set forth in the Detailed Description below.

BRIEF DESCRIPTION OF THE DRAWINGS

FIGS. 3(a) and 3(b) show bread made using non-encapsulated chitosan material, while FIGS. 3(c) and 3(d) show bread made using microencapsulated chitosan material of the present disclosure. The bread made using the microencapsulated chitosan material (chitosan salt) has a lighter loaf color, a higher rise (10 cm versus 9 cm), and a lower density due to less water retention (912 g versus 923 g).

DETAILED DESCRIPTION

Figure 1:
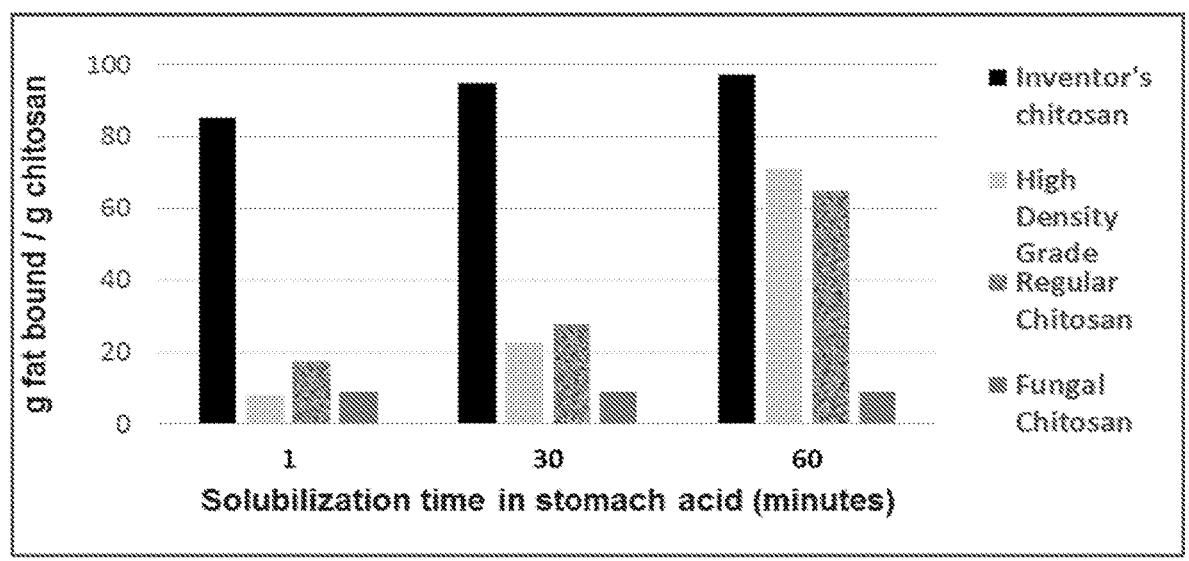
FIG. 1 demonstrates the effect of solubilization time in stomach acid (0.16 N HCl) on the fat-binding capacity of different chitosan products on the market compared to the chitosan product employed in the practice of the present invention. In each set of four bar graphs, the far left bar refers to the chitsan material of the present disclosure, the second bar from the left refers to high-density grade chitosan, the third bar from the left refers to regular-grade chitosan, and the far right bar refers to fungal chitosan.

In accordance with the present disclosure, there are provided chitosan-containing formulations, methods of making such formulations, and methods of using such formulations. Application of a microencapsulation coating on chitosan materials and formulations containing same renders possible the use of chitosan materials for different applications and controls the bioactivity thereof, relying largely on the physical interaction between this cationic molecule and the negative charge of the other component(s) being attracted thereto under acidic conditions.

Thus, in accordance with certain aspects, the present invention provides methods to microencapsulate highly effective chitosan or chitosan salts to counteract their interaction with food components under acidic food environment (pH 3 to 6) and mask any off-flavors and off-tastes, but still allows rapid chitosan solubilization under gastric acid conditions (pH 1-2), leading to the entrapment of simultaneously ingested fat in the digestive tract. This entrapment under gastric environment is converted to a chitosan-fat emulsion upon entering the intestine, as pH is raised to above 6.5, becoming resistant to digestion and absorption.

Chitosan or chitosan salts contemplated for use herein include chitosan succinate, chitosan adipate, chitosan chloride, chitosan glutamate, chitosan lactate, chitosan aspartate, chitosan acetate, chitosan pyruvate, chitosan malate, and the like.

Microencapsulated chitosan (or salts thereof) can be used in different applications, specifically functional foods or formulations where the addition of the microencapsulated product will not interfere with the food components nor reduce the food sensory properties. Such use, in either lipid-rich foods or formulations to reduce their caloric value or a vector food having the role to introduce chitosan during a meal to provide fiber supplementation and/or contribute to the low fat absorption by the body during a meal, is contemplated in this invention. Another alternative use considers the development of new chitosan-based dietary supplements where taste-masking and protection of the microencapsulated chitosan is beneficial.

Therefore, in certain aspects and embodiments, the present disclosure contemplates formulations comprising microencapsulated chitosan (or salts thereof). Note that, as used herein, formulations can include any composition, whether or not in a finished or marketable form. Also note that microencapsulated refers to a material contained within an encapsulating coating, wherein 95% of the encapsulated particles have a particle size of less than 450 μm, or less than 250 μm.

In certain aspects and embodiments, the present disclosure contemplates formulations consisting essentially of microencapsulated chitosan (or salts thereof).

In some aspects, formulations contemplated herein comprise 0.1-10 wt % microencapsulated chitosan (or salts thereof); in some aspects, formulations contemplated herein comprise 0.1-30 wt % microencapsulated chitosan (or salts thereof); in some aspects, formulations contemplated herein comprise 0.1-50 wt % microencapsulated chitosan (or salts thereof); in some aspects, formulations contemplated herein comprise 0.1-70 wt % microencapsulated chitosan (or salts thereof); in some aspects, formulations contemplated herein comprise 0.1-80 wt % microencapsulated chitosan (or salts thereof); in some aspects, formulations contemplated herein comprise 0.1-90 wt % microencapsulated chitosan (or salts thereof); in some aspects, formulations contemplated herein comprise 0.1-95 wt % microencapsulated chitosan (or salts thereof); in some aspects, formulations contemplated herein comprise 0.1-99 wt % microencapsulated chitosan (or salts thereof).

In some aspects, formulations contemplated herein consist essentially of 0.1-10 wt % microencapsulated chitosan (or salts thereof); in some aspects, formulations contemplated herein consist essentially of 0.1-30 wt % microencapsulated chitosan (or salts thereof); in some aspects, formulations contemplated herein consist essentially of 0.1-50 wt % microencapsulated chitosan (or salts thereof); in some aspects, formulations contemplated herein consist essentially of 0.1-70 wt % microencapsulated chitosan (or salts thereof); in some aspects, formulations contemplated herein consist essentially of 0.1-80 wt % microencapsulated chitosan (or salts thereof); in some aspects, formulations contemplated herein consist essentially of 0.1-90 wt % microencapsulated chitosan (or salts thereof); in some aspects, formulations contemplated herein consist essentially of 0.1-95 wt % microencapsulated chitosan (or salts thereof); in some aspects, formulations contemplated herein consist essentially of 0.1-99 wt % microencapsulated chitosan (or salts thereof).

In some embodiments of the aspects and embodiments described herein, the formulation includes a polyol.

In some embodiments of the aspects and embodiments described herein, the formulation includes one or more types of fiber components or nutrients.

In some embodiments of the aspects and embodiments described herein, the formulation represents the inclusion of the microencapsulated chitosan (or salts thereof) into a current food product, at a rate of 0.1-5 wt %; or at a rate of 0.3-2 wt %; or at a rate of 0.5-1 wt %, or the like, to develop new functional or medical foods.

In some aspects, the present disclosure contemplates methods for making the above-described formulations, said methods comprising (a) applying a suitable coating to finely divided chitosan material (or salts thereof) under conditions suitable to create a shell microencapsulating the chitosan material, as pure chitosan or as a salt, thereby protecting same: (b) subjecting the resulting chitosan-coating material combination to conditions suitable to achieve interaction between the finely divided chitosan material and the coating material, (c) optionally rinsing the microencapsulated chitosan product to remove any excess coating material, followed by (d) a batch or continuous drying process, thereby producing a powder, granules or pellets for wide applications in functional foods and/or dietary supplements.

As used herein, the term "granule" refers to a plurality of particles aggregated into a more or less spherical shape.

As employed herein, a "microcapsule" refers to a shell prepared from a coating material to enclose a core material which is intended to be protected until released. A variety of coating materials can be employed herein.

Exemplary coating materials contemplated for use herein include aqueous solutions of shellac (dewaxed and decolorized), cellulose derivatives (e.g., carboxymethylcellulose or ethylcellulose), carbohydrates, polysaccharide gums, polyvinyl alcohol, polyvinyl acetate, polyvinyl pyrrolidone, polymethylacrylate, zein, and the like.

In vitro testing of invention materials has shown that binding of fat by such chitosan products under gastric conditions can be as much as 50 times their weight and up to about 150 times, or up to about 165 times, which is outstanding compared to other current chitosan or fiber products on the market. And importantly, this can be achieved after only a short solubilization time of 1 to 5 minutes in gastric acid.

FIG. 1 demonstrates the effect of solubilization time in stomach acid (0.16N HCl) on the fat-binding capacity of different chitosan products on the market compared to products according to the present invention. This implies that a rapid solubilizing chitosan product does not need to be taken long before a meal to act as an effective fat binder. It can conveniently be taken just before, or even during, the meal.

Table 1 presents the fat-binding capacity of exemplary currently available chitosan or fat-binder products on the market in comparison to the products contemplated by the present invention, using the five-minute fat-binding test (standard test used as a quality control procedure).

TABLE 1

Fat-binding products currently available on the market

| Product | Main component | Fat-binding capacity* (g oil/g product) |
|---|---|---|
| Oenobiol Liporéducteur | Fungal chitosan | 5 +/− 0 |
| NS Gestor de Grasas | Fungal chitosan | 6.5 +/− 3.5 |
| Fat Control | Fungal chitosan | 10 +/− 0 |
| XLS Medical | Litramine ™ | 4 +/− 1 |
| Liposinol | Litramine ™ | 5 +/− 0 |
| L112 | Chitosan | 10 +/− 1 |
| Fat Magnet | Chitosan, psyllium husk, ascorbic acid | 14.5 +/− 0.5 |
| Chitomar | Chitosan, microcrystalline cellulose, ascorbic acid | 17.5 +/− 6.5 |
| LipoCaptur | Chitosan | 19 +/− 0 |
| Appetite Control | High swelling capacity plant fiber | 24 +/− 0 |
| Invention products | Chitosan | 99 up to 165 |

*evaluated by the five-minute fat-binding test using 10.0 g corn oil

The data presented in Table 1 demonstrate the superior efficacy of the invention chitosan products in binding fat, mimicking the digestive tract environment, binding from about 4 times up to about 40 times more than competitors' products.

By microencapsulating chitosan, the fat-binding capacity, or any other interaction with other food components, is restricted and any off-flavors and off-tastes become reduced or totally masked. Such protection of highly efficient fat-binding chitosan products allows new applications for the food industry, e.g. their use in functional foods or new types of chitosan-based dietary supplements, because any off-flavors and off-tastes will be minimized, but still providing a great fat-binding capacity of the fat ingested during the meal once in the stomach. Table 2 illustrates one of the many advantages of microencapsulating chitosan, i.e., limiting the interaction thereof with food at food pH.

TABLE 2

Fat-binding test* (gram oil/gram chitosan) based on corn oil (10.0 g) added to 0.1 g solubilized chitosan (dry basis)

| Acid environment | Chitosan salt | Microencapsulated chitosan |
|---|---|---|
| pH 1-2 | 99 | 99 |
| pH 3-4 | 22 | 1 |

*maximal fat-binding of the standard test is 100 g oil/g chitosan

The instant disclosure further provides methods for treating or preventing diseases or disorders, or for maintaining a healthy or good condition, or the like, for example by local administration of the formulations as described herein.

A patient or subject to be treated by any of the compositions or methods of the present disclosure can mean either a human or a non-human animal. In an embodiment, the present disclosure provides methods for the treatment of a disease or disorder in a human patient in need thereof. In an embodiment, the present disclosure provides methods for the treatment of digestive disorders in a human patient in need thereof. In another embodiment, the present disclosure provides methods for the treatment of a disease in a veterinary patient in need thereof, including, but not limited to dogs, horses, cats, rabbits, gerbils, hamsters, rodents, birds, aquatic mammals, cattle, pigs, camelids, and other zoological animals.

The term "treating" refers to preventing a disease, disorder or condition from occurring in a cell, a tissue, a system, animal or human which may be predisposed to the disease, disorder and/or condition but has not yet been diagnosed as having it; stabilizing a disease, disorder or condition, i.e., arresting its development; and/or relieving one or more symptoms of the disease, disorder or condition, i.e., causing regression of the disease, disorder and/or condition.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

Accordingly, in some aspects and embodiments of the present disclosure, there are provided methods of treating or preventing a disease or condition, that includes orally administering a formulation of any of the aspects or embodiments as disclosed herein.

In accordance with the present invention, there are provided methods of producing microencapsulated chitosan suitable for oral intake from finely divided chitosan material, said methods comprising:
  (a) applying a suitable coating to said finely divided chitosan material under conditions suitable to create a shell microencapsulating the chitosan material, as pure chitosan or as a salt, thereby protecting same,
  (b) subjecting the resulting chitosan-coating material combination to conditions suitable to achieve interaction between the finely divided chitosan material and the coating material,
  (c) optionally rinsing the microencapsulated chitosan product to remove any excess coating material, followed by (d) a batch or continuous drying process, thereby producing a powder, granules or pellets for wide applications in functional foods and/or dietary supplements.

In accordance with some aspects and embodiments of the present invention, the coating material adheres to said finely divided chitosan material by ionic bonding or by any other non-covalent means, e.g., hydrogen bonding, van der Waals forces, and the like.

In accordance with some aspects and embodiments of the present invention, the coatings contemplated herein are applied to the chitosan material by batch or continuous wet processing, spraying, spray drying, fluid bed coating, air-suspension coating, and the like.

In accordance with some aspects and embodiments of the present invention, the microencapsulated chitosan masks any off-taste of said chitosan material.

In accordance with some aspects and embodiments of the present invention, the microencapsulated chitosan reduces the interaction of said chitosan material with other food components or ingredients, thereby maintaining the desirable food sensory properties of the other food components or ingredients.

In accordance with some aspects and embodiments of the present invention, the microencapsulated chitosan controls the release of said chitosan material under varying acidic conditions.

In accordance with some aspects and embodiments of the present invention, the chitosan material is only substantially released in stomach acid.

In accordance with some aspects and embodiments of the present invention, the chitosan is obtained from crustacean chitin and is optionally used as a chitosan salt.

In accordance with some aspects and embodiments of the present invention, the chitosan employed for the preparation of said microencapsulated chitosan has an average molecular mass of from about 100,000 Daltons to about 1,000,000 Daltons; in accordance with some aspects and embodiments of the present invention, the chitosan employed for the preparation of said microencapsulated chitosan has an average molecular mass of from about 150,000 Daltons to about one 750,000 Daltons; in accordance with some aspects and embodiments of the present invention, the chitosan employed for the preparation of said microencapsulated chitosan has an average molecular mass of from about 150,000 Daltons to about 500,000 Daltons; in accordance with some aspects and embodiments of the present invention, the chitosan employed for the preparation of said microencapsulated chitosan has an average molecular mass of from about 200,000 Daltons to about 400,000 Daltons.

Chitosan contemplated for use herein can be characterized in a variety of ways. For example, 1% of chitosan on a dry basis, in 1% acetic acid, may have a Brookfield rotational viscosity at 25° C. from about 5 cps to about 2,000,000 cps; in some embodiments, chitosan employed herein may have a Brookfield rotational viscosity at 25° C. from about 5 cps-10,000 cps; in some embodiments, chitosan employed herein may have a Brookfield rotational viscosity at 25° C. from about 5 cps-50,000 cps; in some embodiments, chitosan employed herein may have a Brookfield rotational viscosity at 25° C. from about 5 cps-100,000 cps; in some embodiments, chitosan employed herein may have a Brookfield rotational viscosity at 25° C. from about 5 cps-200,000 cps; in some embodiments, chitosan employed herein may have a Brookfield rotational viscosity at 25° C. from about 5 cps-300,000 cps; in some embodiments, chitosan employed herein may have a Brookfield rotational viscosity at 25° C. from about 5 cps-400,000 cps; in some embodiments, chitosan employed herein may have a Brookfield rotational viscosity at 25° C. from about 5 cps-500,000 cps; in some embodiments, chitosan employed herein may have a Brookfield rotational viscosity at 25° C. from about 5 cps-600,000 cps; in some embodiments, chitosan employed herein may have a Brookfield rotational viscosity at 25° C. from about 5 cps-700,000 cps; in some embodiments, chitosan employed herein may have a Brookfield rotational viscosity at 25° C. from about 5 cps-800,000 cps; in some embodiments, chitosan employed herein may have a Brookfield rotational viscosity at 25° C. from about 5 cps-900,000 cps; in some embodiments, chitosan employed herein may have a Brookfield rotational viscosity at 25° C. from about 5 cps-1,000,000 cps; in some embodiments, chitosan employed herein may have a Brookfield rotational viscosity at 25° C. from about 5 cps-1,100,000 cps; in some embodiments, chitosan employed herein may have a Brookfield rotational viscosity at 25° C. from about 5 cps-1,200,000 cps; in some embodiments, chitosan employed herein may have a Brookfield rotational viscosity at 25° C. from about 5 cps-1,300,000 cps; in some embodiments, chitosan employed herein may have a Brookfield rotational viscosity at 25° C. from about 5 cps-1,400,000 cps; in some embodiments, chitosan employed herein may have a Brookfield rotational viscosity at 25° C. from about 5 cps-1,500,000 cps; in some embodiments, chitosan employed herein may have a Brookfield rotational viscosity at 25° C. from about 5 cps-1,600,000 cps; in some embodiments, chitosan employed herein may have a Brookfield rotational viscosity at 25° C. from about 5 cps-1,700,000 cps; in some embodiments, chitosan employed herein may have a Brookfield rotational viscosity at 25° C. from about 5 cps-1,800,000 cps; in some embodiments, chitosan employed herein may have a Brookfield rotational viscosity at 25° C. from about 5 cps-1,900,000 cps; in some embodiments, chitosan employed herein may have a Brookfield rotational viscosity at 25° C. from about 5 cps-2,000,000 cps; and the like.

In accordance with some aspects and embodiments of the present invention, the chitosan employed for the preparation of said microencapsulated chitosan has a Brookfield rotational viscosity of from about 10-10,000 cps; in some aspects and embodiments of the present invention, the chitosan employed for the preparation of said microencapsulated chitosan has a Brookfield rotational viscosity of from about 20-2,000 cps; in some aspects and embodiments of the present invention, the chitosan employed for the preparation of said microencapsulated chitosan has a Brookfield rotational viscosity of from about 50-1000 cps.

In accordance with some aspects and embodiments of the present invention, the chitosan employed for the preparation of said microencapsulated chitosan is in the form of particles having a particle size of at least about 50 mesh; in some aspects and embodiments of the present invention, the chitosan employed for the preparation of said microencapsulated chitosan is in the form of particles having a particle size of at least about 100 mesh up to about 200 mesh.

In accordance with some aspects and embodiments of the present invention, the chitosan employed for the preparation of said microencapsulated chitosan has a percentage of deacetylation of from about 65% to about 98%.

In accordance with some aspects and embodiments of the present invention, the chitosan employed for the preparation of said microencapsulated chitosan has a percentage of deacetylation of from about 70% to about 90%.

In accordance with some aspects and embodiments of the present invention, the chitosan employed for the preparation of said microencapsulated chitosan undergoes rapid acid solubilization in stomach acid (0.16N HCl), i.e., within 5 minutes at a pH <2, leading to a high fat-binding capacity (>50 g oil/g chitosan).

In accordance with some aspects and embodiments of the present invention, the effective amount of coating comprises in the range of about 5-25 percent of the weight of the chitosan with which the coating is mixed.

In accordance with some aspects and embodiments of the present invention, the effective amount of coating comprises at least about 10 percent of the weight of the chitosan with which the coating is mixed.

In accordance with some aspects and embodiments of the present invention, any of the coatings contemplated for use herein can be characterized as being one or more of the following, i.e.,
  relatively neutral and tasteless,
  not causing mouth astringency,
  not undesirably changing the colour of chitosan,
  being stable at pH >3 while rapidly solubilizing or releasing the core material at pH <2, and/or
  tolerating process heating up to about 80° C.

In accordance with some aspects and embodiments of the present invention, the mixture of chitosan and coating is optionally supplemented with a low level of a rheology modifier (e.g., xanthan gum, guar gum, or the like) to facilitate a spray drying process.

In accordance with some aspects and embodiments of the present invention, the mixture of chitosan, coating and optional additional ingredient(s) is dried to a moisture content of from substantially 0% moisture to about 10% moisture.

In accordance with some aspects and embodiments of the present invention, there are provided chitosan materials produced by any of the methods described herein.

In accordance with some aspects and embodiments of the present invention, the microencapsulation/coating of chitosan materials contemplated for use herein has a neutral molecular charge once applied to the core material.

In accordance with some aspects and embodiments of the present invention, the microencapsulation/coating of chitosan materials contemplated for use herein has a light colour which is substantially the same as that of the chitosan raw material used.

In accordance with some aspects and embodiments of the present invention, the microencapsulation/coating of chitosan materials contemplated for use herein withstands a temperature up to and including 80° C. for a constant time of at least 1 minute; in some embodiments, the microencapsulation/coating thereof withstands a temperature up to and including 85° C. for a constant time of at least 1 minute; in some embodiments, the microencapsulation/coating thereof withstands a temperature up to and including 90° C. for a constant time of at least 1 minute; in some embodiments, the microencapsulation/coating thereof withstands a temperature up to and including 95° C. for a constant time of at least 1 minute; in some embodiments, the microencapsulation/coating thereof withstands a temperature up to and including 100° C. for a constant time of at least 1 minute.

In accordance with some aspects and embodiments of the present invention, the microencapsulation/coating of chitosan materials contemplated for use herein:
  withstands acidic conditions of pH 3 and above, but solubilizes rapidly or releases the core material at a pH below pH 2.

In accordance with some aspects and embodiments of the present invention, the microencapsulation/coating of chitosan materials contemplated for use herein solubilizes (and/or allows the chitosan to solubilize) in less than 5 min in acid below pH 2.

In accordance with some aspects and embodiments of the present invention, the microencapsulation/coating of chitosan materials contemplated for use herein is further characterized as having a high fat-binding capacity (>50 g corn oil/g microencapsulated chitosan).

In accordance with some aspects and embodiments of the present invention, the microencapsulation/coating of chitosan materials contemplated for use herein is quickly released under very acidic environment (pH <2), thereby causing the chitosan material to become positively charged.

In accordance with some aspects and embodiments of the present invention, the microencapsulation/coating of chitosan materials contemplated for use herein can be used for the production of a wide variety of products, e.g.:
  a. New types of chitosan-based dietary food supplements (to reduce caloric intake of food consumed and/or as a fiber supplement),
  b. Boost drinks,
  c. Protein drinks,
  d. Protein powders,
  e. Snackbars and health bars,
  f. Meal-replacers,
  g. and the like, as well as combinations of any two or more thereof.

As used herein, the term "dietary supplement" refers to products intended for ingestion that contain a "dietary ingredient" intended to add further nutritional value to or supplement the diet. Some dietary supplements can contribute to an adequate dietary intake of essential nutrients; others may help reduce risk of disease. Dietary supplements are very often in the form of tablets, capsules and/or softgels, gelcaps, liquids, powders, and the like. New types of dietary food supplements are considered as less conventional and can be designed to be convenient and include several nutrients, in the form of liquid, gel, portioned powder/granules or provided into a container and to be portioned by the end-user.

In accordance with some aspects and embodiments of the present invention, the microencapsulation/coating of chitosan materials contemplated for use herein can be used as a food ingredient in one or more of:
  i. Cold sauces,
  ii. Warm sauces,
  iii. Gravies,
  iv. Mayonnaise and related products,
  v. Tartar sauce,
  vi. Hamburger sauce,
  vii. Dairy products,
  viii. Cream and cream products,
  ix. Desserts, puddings and confectionaries,
  x. Bread, cakes, cookies, pancakes and waffles,
  xi. and the like, as well as combinations of any two or more thereof.

In accordance with some aspects and embodiments of the present invention, there are provided microencapsulated chitosan materials characterized as:
  light yellow to brown free flowing powder or granules,
  pH 6-7 (1% solution),
  bulk density >0.2 up to about 0.5 g/cm$^3$,
  fat-binding capacity >50 g corn oil/g microencapsulated product; or at least 50 times its weight (or 5000%),
  contains at least 70% chitosan, max 95% on a dry basis,
  particle size at least 95%<250 μm for fine powder or coarser (250-450 μm) for other uses/purposes, can be suspended in water, but is non water soluble,
tolerates up to 80° C. or higher for a few minutes (for a short time period before melting),
neutral taste and odour; and/or
little or no aftertaste.

As used herein in connection with numerical values, the terms "approximately" and "about" mean +/−10% of the indicated value, including the indicated value.

As readily recognized by those of skill in the art, the amount of chitosan present in the formulations contemplated herein can vary widely, typically falling in the range of about 0.1% and about 10% by weight based on the weight of said formulation. In some embodiments, the chitosan concentration falls in the range of about 0.5-5%; in some embodiments, the chitosan concentration falls in the range of about 0.7-4%; in some embodiments, the chitosan concentration falls in the range of about 1-3%.

Chitosan materials contemplated for use herein can be further characterized by the percentage of deacetylation of said chitosan, which in some embodiments can be up to 98%; in some embodiments, the chitosan has a percentage of deacetylation from about 65 up to about 98%; in some embodiments, the chitosan has a percentage of deacetylation from about 70 up to about 98%; in some embodiments, the chitosan has a percentage of deacetylation from about 75 to about 98%; in some embodiments, the chitosan has a percentage of deacetylation from about 80 up to about 98%.

In some embodiments, chitosan contemplated for use herein is of any source of animal or microbial or fungal origin; in some embodiments, chitosan contemplated for use herein is of crustacean origin.

Chitosan materials contemplated for use herein can be further characterized with reference to one or more of the following:
    a moisture content of <15%;
    an ash content <1%,
    a turbidity of <50 NTU,
    a solubility of >99%,
    a high fat-binding capacity, binding at least 50 g oil/g chitosan, and/or
    <3 ppm heavy metals (i.e., As, Cd, Pb, Hg).
Chitosan materials which meet a plurality of the above-referenced criteria are also referred to herein as "high quality" chitosan.

As readily recognized by those of skill in the art, moisture content can be determined by a moisture analyser; ash content (on a dry basis) can be determined in a variety of ways, e.g., by dry ashing at 800° C. for 3 h, or similar method; turbidity can be determined by measuring turbidity of 1% chitosan (dry basis) in 1% acetic acid; and total heavy metals (As, Cd, Pb, Hg) can be determined by ICP/MS (USP730).

In some embodiments of the present invention, there are provided chitosan-containing formulations prepared by any of the methods described herein.

Additional Formulation Ingredients

The formulations of the present disclosure may also contain other components such as, but not limited to, food additives, food ingredients, polyols, preservatives, and the like, as required in current food products designed to be improved or developed into functional or medical foods by the inclusion of the microencapsulated chitosan. It should be appreciated that the compositions of the present disclosure may require pH adjustment with a suitable acidic component in accordance with the acidity level required in the food for its palatability, quality, safety and shelf life.

Polyols contemplated for use herein typically have a molecular weight in the range of about 90-1000 g/mol; in some embodiments, the polyol has a molecular weight in the range of about 92-700 g/mol. Exemplary polyols include glycerol, PPG, PEG, maltitol, sorbitol, xylitol, and the like, as well as mixtures of any two or more thereof.

As readily recognized by those of skill in the art, the concentration of polyol can vary widely. For example, in some embodiments, the concentration of said polyol falls in the range of about 0.1-10%; in some embodiments, the concentration of said polyol falls in the range of about 0.5-10%; in some embodiments, the concentration of said polyol falls in the range of about 1-5% (w/w) of said formulation.

The following examples are provided to further illustrate aspects of the invention. These examples are non-limiting and should not be construed as limiting any aspect of the invention.

Example 1

Preparation and Uses of Microencapsulated Chitosan-Containing Formulations

Microencapsulated chitosan-containing formulations are prepared as follows. High fat-binding chitosan or chitosan salt as the core material of a mesh size of about 100 mesh is dispersed into a strong alkaline coating solution containing shellac, stirring the mixture for 15 min at room temperature, after which any excess coating agent is removed by decantation, a step repeated 2-3 times after successive rinsing steps. The concentrated coated chitosan material is kept suspended in solution by adding a minimal amount of xanthan gum, after which it can be atomized by spray drying to achieve a fine powder of microencapsulated chitosan of about 70 mesh (US size) with a moisture content of about 5-6%. The material is packaged after sieving and stored in a cool dry place until prepared into a new type of chitosan-based dietary supplement or formulated functional product, as descried herein.

In most formulations, a concentration of 0.3-1% (w/w) of the microencapsulated chitosan powder in the final product is desirable. This microencapsulated product suits well water-based, neutral products and is appropriate in different functional food formulations. A dietary supplement or food portion providing about 500-1000 mg of the microencapsulated chitosan fiber may contribute to digestive health and/or overall health, especially if eaten on a regular basis, at least once to twice a day.

Example 2

Preparation and Uses of Additional Microencapsulated Chitosan-Containing Formulations Additional chitosan-containing formulations are prepared as follows. Using an air-suspension coating technique, a 10% coating solution of carboxymethylcellulose is applied onto chitosan powder particles in a batch or continuous process, by suspending the particles by an air stream at 30-70° C. and spraying them with the atomized coating material. A coating layer is applied until the chitosan powder is properly microencapsulated and aggregated, resulting in microencapsulated chitosan granules of about 40 mesh (US size) with a moisture content of about 3-5% by weight. The material is packaged after sieving and stored in a cool dry place until prepared into a new type of chitosan-based dietary supplement or formulated functional product, as described herein.

In most formulations, a concentration of 0.3-1% (w/w) of the microencapsulated chitosan granules in the final product is desirable. This microencapsulated product suits well sour foods and dairy products and is appropriate in different functional food formulations. A dietary supplement or food portion providing about 500-1000 mg of the microencapsulated chitosan fiber may contribute to digestive health and/or overall health, especially if eaten on a regular basis, at least once to twice a day.

Example 3

Preparation and Use of Additional Microencapsulated Chitosan-Containing Formulations Additional chitosan-containing formulations are prepared as follows. Microencapsulated chitosan can be added to various fatty food products to reduce their caloric value upon digestion, for example chocolate milk (0.5% w/w), chocolate pudding (1.0% w/w), filling of fine chocolate (1.0% w/w), dairy desserts (0.8% w/w), salad dressing (1.0% w/w), hamburger sauce (1.0% w/w) and sandwich spread (0.5% w/w), to name a few. Such addition implies to perform necessary adjustments of previous food formulations to ensure a proper acidity level as required for palatability, quality, safety and shelf life of the functional food products developed. A food portion providing about 500-1000 mg of the microencapsulated chitosan fiber may contribute to digestive health and/or overall health, especially if eaten on a regular basis, at least once to twice a day.

Example 4

Microencapsulated Chitosan Salt with Xanthan Gum

Figure 2:
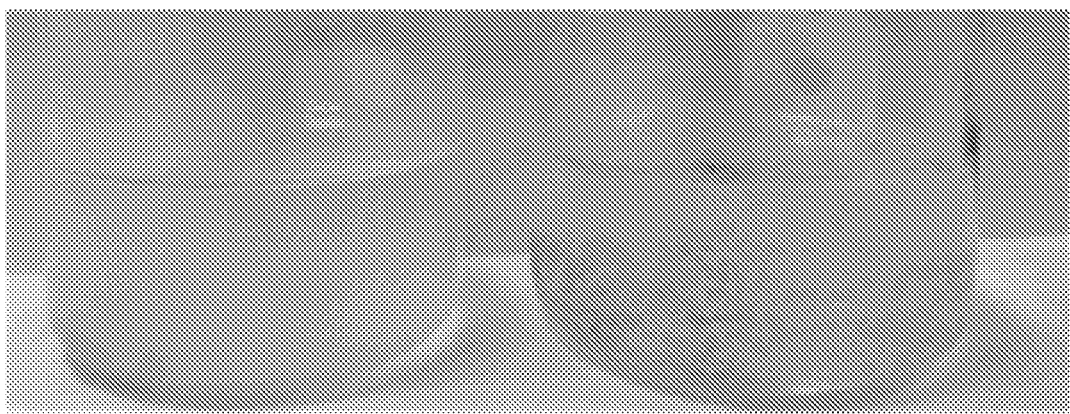
FIG. 2 shows photographs that compare xanthan gum preparations using a non-microencapsulated chitosan salt with xanthan gum preparations using a microencapsulated chitosan salt. The two beakers shown in the photo are for chitosan salt compositions having 0.25% (w/w) chitosan salt and 0.12% (w/w) xanthan gum. The beaker on the left employed a microencapsulated chitosan material (chitosan salt), and the beaker on the right employed a non-encapsulated chitosan material (chitosan salt).

An example of food ingredient interaction with chitosan or chitosan salts is xanthan gum, an anionic polysaccharide, which in its presence (0.12% w/w) will aggregate to chitosan or chitosan salts (0.25% w/w) under mild acidic food condition. This may lead to undesirable textural defects in food products and well as decreased palatability. FIG. 2 shows a photo comparing xanthan gum preparations using non-microencapsulated chitosan salt and microencapsulated chitosan salt, in the above concentrations.

Example 5

Microencapsulated Chitosan Salt with Bread

Ingredients: 300 g wheat flour+100 g coarse spelt flour+ 100 g whole wheat flour+65 g oat flakes; 5 g sugar+1 teaspoon salt+15 g butter+9 g yeast+1 tablespoon grated parmesan+390 g water; 12 g regular chitosan or microencapsulated chitosan salt (about 2% of dry ingredients).

Figure 3:
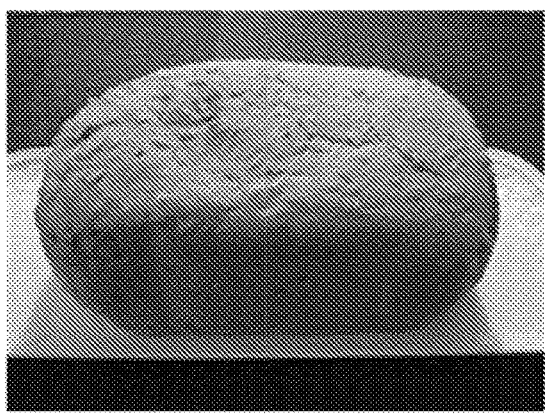
FIG. 3 shows photographs that compare bread made using non-microencapsulated chitosan salt with bread made using microencapsulated chitosan salt. The four photographs show bread made using a chitosan material (chitosan salt) at 2% w/w.
Figure 3:
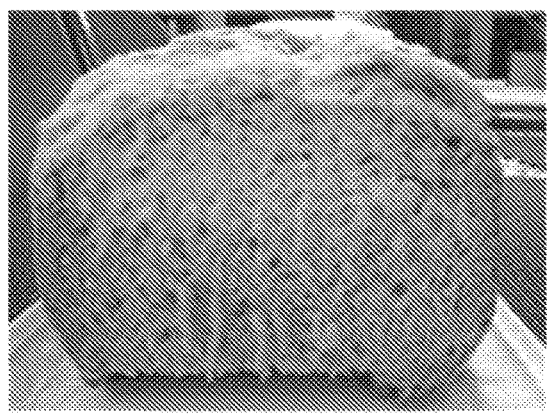
Figure 3:
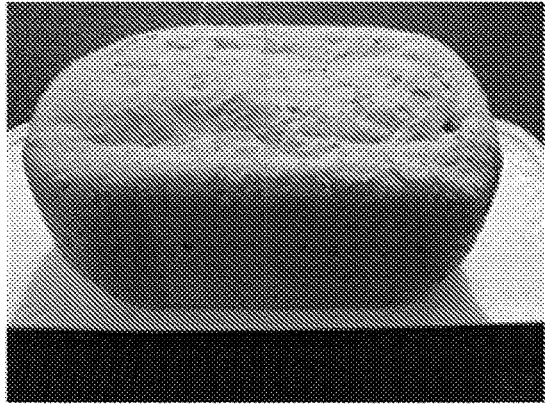
Figure 3:
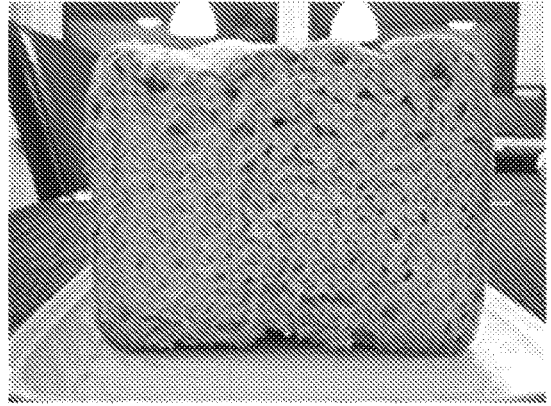

A chitosan salt product (either in its regular form or microencapsulated) was added to a bread dough at a rate of about 2% (w/w). After baking in a breadmaker, it was observed that the regular chitosan salt became involved with the other ingredients, retaining more water (observed by higher weight, 923 g) in the loaf, reducing its volume expansion (lower height, ca 9 cm) and enhancing its colour (darker due to Maillard reaction), in agreement with published literature. The microencapsulated chitosan salt was protected by its coating and did not apparently become involved with other ingredients, as demonstrated by its higher loaf height (ca 10 cm), lighter colour and weight (912 g). FIG. 3 shows a photo comparing bread made with non-microencapsulated chitosan salt and bread made using microencapsulated chitosan salt.

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

The invention claimed is:

1. A plurality of microencapsulated chitosan particles comprising
   (a) a core comprising a chitosan or a chitosan salt, and
   (b) a shell enclosing the core, wherein the shell comprises a coating material;
   wherein the coating material comprises shellac, a cellulose derivative, a carbohydrate, a polysaccharide gum, polyvinyl alcohol, polyvinyl pyrrolidone, or zein,
   wherein the weight of the coating material is in the range of from about 5 to about 25% of the weight of the chitosan or chitosan salt;
   wherein at least 95% of the microencapsulated chitosan particles have a particle size of less than 250 μm;
   wherein the coating material is insoluble under acidic conditions of pH 3 or above, but solubilizes or releases the core material within 5 minutes at pH <2, thereby causing the chitosan material to become positively charged;
   wherein the particles have a fat binding capacity of at least 50 g oil/g chitosan at pH <2.

2. A plurality of microencapsulated chitosan particles comprising
   (a) a core comprising a chitosan or a chitosan salt, and
   (b) a shell enclosing the core, wherein the shell comprises a coating material;
   wherein the chitosan or chitosan salt in the core comprises a particle size of at least about 100 mesh;
   wherein the weight of the coating material is in the range of from about 5 to about 25% of the weight of the chitosan or chitosan salt;
   wherein at least 95% of the microencapsulated chitosan particles have a particle size of less than 250 μm;
   wherein the coating material is insoluble under acidic conditions of pH 3 or above, but solubilizes or releases the core material within 5 minutes at pH <2, thereby causing the chitosan material to become positively charged;
   wherein the particles have a fat binding capacity of at least 50 g oil/g chitosan at pH <2.

3. The microencapsulated chitosan particles of claim 1, wherein the chitosan or chitosan salt in the core comprises a particle size of from about 100 mesh to about 200 mesh.

4. The microencapsulated chitosan particles of claim 1, wherein the chitosan or chitosan salt comprises chitosan succinate, chitosan adipate, chitosan chloride, chitosan glutamate, chitosan lactate, chitosan aspartate, chitosan acetate, chitosan pyruvate, or chitosan malate.

5. The microencapsulated chitosan particles of claim 1, wherein the chitosan or chitosan salt is of crustacean origin.

6. The microencapsulated chitosan particles of claim 1, wherein the chitosan or chitosan salt has an average molecular mass of from about 100,000 Daltons to about 1 million Daltons.

7. The microencapsulated chitosan particles of claim 1, wherein the chitosan or chitosan salt has a Brookfield rotational viscosity at 25° C. of from about 10 cps to about 10,000 cps.

8. The microencapsulated chitosan particles of claim 1, wherein the chitosan or chitosan salt has a percentage of deacetylation of from about 70% to about 90%.

9. The microencapsulated chitosan particles of claim 2, wherein the weight of the coating material is about 10% of the weight of the chitosan or chitosan salt, and wherein the coating material adheres to the core non-covalently.

10. The microencapsulated chitosan particles of claim 2, wherein the coating material comprises shellac, a cellulose derivative, a carbohydrate, a polysaccharide gum, polyvinyl alcohol, polyvinyl pyrrolidone, or zein.

11. The microencapsulated chitosan particles of claim 10, wherein the cellulose derivative is carboxymethylcellulose or ethylcellulose.

12. The microencapsulated chitosan particles of claim 1, wherein the particles are in the form of a powder, granules, or pellets.

13. The microencapsulated chitosan particles of claim 1, wherein the particles have a moisture content of 0% to 10%.

14. The microencapsulated chitosan particles of claim 1, wherein the particles have a fat binding capacity of at least 100 times the weight of chitosan or chitosan salt at a pH of about 2.

* * * * *